United States Patent [19]

Reinherz et al.

[11] 4,443,427

[45] Apr. 17, 1984

[54] MONOCLONAL ANTIBODY

[75] Inventors: Ellis L. Reinherz, Lincoln; Stuart F. Schlossman, Newton Centre, both of Mass.

[73] Assignee: Sidney Farber Cancer Institute, Inc., Boston, Mass.

[21] Appl. No.: 390,548

[22] Filed: Jun. 21, 1982

[51] Int. Cl.³ .................... A61K 43/00; A61K 39/00; C12N 15/00
[52] U.S. Cl. .................... 424/1.1; 436/548; 435/68; 435/172; 128/1.1; 424/85
[58] Field of Search .................. 436/548; 424/1, 85; 128/1.1; 435/68, 172, 240

[56] References Cited

U.S. PATENT DOCUMENTS

| | | | |
|---|---|---|---|
| 4,196,265 | 4/1980 | Koprowski et al. | 435/2 |
| 4,331,647 | 5/1982 | Goldenberg | 424/1 |
| 4,348,376 | 9/1982 | Goldenberg | 424/1 |
| 4,361,549 | 11/1982 | Kung et al. | 424/85 |
| 4,361,550 | 11/1982 | Kung et al. | 424/85 |
| 4,363,799 | 12/1982 | Kung et al. | 424/85 |
| 4,364,932 | 12/1982 | Kung et al. | 424/85 |
| 4,364,933 | 12/1982 | Kung et al. | 424/85 |
| 4,364,935 | 12/1982 | Kung et al. | 424/85 |
| 4,364,936 | 12/1982 | Kung et al. | 424/85 |
| 4,364,937 | 12/1982 | Kung et al. | 424/85 |
| 4,376,110 | 3/1983 | David et al. | 436/513 |
| 4,381,295 | 4/1983 | Kung et al. | 424/85 |

OTHER PUBLICATIONS

Reinherz, E. L. et al., Cell, vol. 30, pp. 735–743, (1982).
Reinherz, E. L. et al., J. Immunology, vol. 123, pp. 1312–1317, (1979).
Kamoun, M. et al., J. Immunology, vol. 127, pp. 987–991, (1981).
Haynes, B. F. et al., Immunological Reviews, vol. 57, pp. 127–161, (1981).
Reinherz, E. L. et al., Cell, vol. 19, pp. 821–827, (1980).
Tsudo, M. et al., J. Immunology, vol. 129, pp. 592–595, (1982).
Reinherz et al., (1980), Cell 19, 821.
Reinherz et al., (1981), J. Clin. Invest. 68, 699.
Reinherz et al., (1979), J. Immunol. 123, 1312.
Ritz et al., (1980), Nature 283, 583.

Primary Examiner—Benjamin R. Padgett
Assistant Examiner—M. Moskowitz

[57] ABSTRACT

Monoclonal antibodies specific to a mature human T cell surface antigen of molecular weight of about 120,000 daltons as determined by electrophoresis, the antigen not being modulated by monoclonal antibodies specific to it and being restricted within the human lymphoid system to the surface of mature T cells, the monoclonal antibodies being capable of selectively binding mature human T cells and rendering them inactive in vivo and failing to induce the proliferation or activation of human lymphocytes.

8 Claims, No Drawings

MONOCLONAL ANTIBODY

The invention described herein was made in the course of work under a grant or award from the National Institutes of Health.

Human T cells are known to possess a number of specific surface antigens which play various roles in T cell function. For example, the surface antigen T3 (Reinherz et al. (1980) Cell 19, 821), which appears in late intrathymic ontogeny, may be important in cell mediated lympholysis.

Monoclonal antibodies have been produced which are specific for particular T cell antigens, and which thus interact with T cells in specific ways. For example, anti-T3 is capable of blocking cell mediated lympholysis, as well as inhibiting T cell proliferative responses to soluble antigen and inducing T cell mitogenesis. Anti-T3 also causes T3 antigen to rapidly modulate from the cell surface, so that T cells which have been incubated with anti-T3 monoclonal antibody lose their ability to react with the antibody.

The surface antigens of T cells change over the course of T cell ontogeny. The stages of T cell differentiation, at least in the murine system, are generally related to the location of the T cells in the thymus; i.e., cortical T cells are generally functionally immature, sensitive to cortisone, express low amounts of H-2 antigen, and react with peanut agglutinin (PNA), while medullary T cells generally are functionally competent (mature) and are unreactive with PNA. This division, however, is probably not absolute; some thymic cortical cells may not simply be immature medullary cells, but may represent a unique T cell sub-population capable of expressing mature T cell antigens. One piece of evidence for this is that some (10–20%) of the PNA reactive (PNA+) cortical cells also react with the monoclonal antibody anti-T1, which reacts only with mature T cells.

Patients with severe combined immunodeficiency (SCID) have major defects in immune function since they generally lack both T as well as B lymphocytes. Clinical manifestations of this defective immunity include early onset of life threatening pulmonary infection, moniliasis, chronic diarrhea and wasting which progressively worsens despite conservative therapies. Although the precise etiology of severe combined immunodeficiency has not been determined, studies have indicated that the circulating lymphoid cells of SCID patients are of two major phenotypes as defined by monoclonal antibody analysis; either T10+T3−T4−T8− or T10+T3+T4+T8+ (Reinherz et al. (1981) J. Clin. Invest. 68, 699). The former population is derived from a precursor bone marrow or early thymocyte compartment whereas the latter represents a late stage of thymocyte differentiation (Reinherz et al. (1980) Cell 19, 821). Only those SCID patients with circulating cells of the more mature T10+T3+T4+T8+ phenotype demonstrate immunologic function.

Corrective therapy for SCID presently requires bone marrow transplantation. Unfortunately, the invariably lethal graft-versus-host disease (GVHD) accompanying transplantation with histoincompatible cells has necessitated donor recipient HLA identity as a prerequisite for transplantation. This has, in effect, denied potentially corrective therapy to the majority of patients (approximately 60%). Moreover, even among the 40% of individuals who are transplanted with donor bone marrow cells matched at HLA A, B and DR loci, there is often some degree of GVHD and/or post-transplant infection.

The present invention provides monoclonal antibodies specific to a particular antigen on the surface of mature human T cells. The unique antigen is designated "T12" and has a molecular weight of about 120,000 daltons, as determined by carrying out electrophoresis on the antigen and comparing its movement with that of marker proteins of known molecular weight. T12 is restricted in the human lymphoid system to the surfaces of mature cells, and also possesses the desirable characteristic of not being modulated off of the surface of T cells when contacted with monoclonal antibody specific to it. This antigen/antibody relationship is one feature which renders the monoclonal antibodies of the invention useful in a variety of medical applications, including the diagnosis and treatment of a number of immune system-related disorders. Other advantages of the anti-T12 monoclonal antibodies of the invention are their ability to selectively bind to mature human T cells and render them inactive in vivo and their failure to induce the proliferation or activation of human lymphocytes.

All monoclonal antibodies having the above characteristics and being specific for the above-defined T12 surface antigen on human T cells are encompassed by the present invention, and are referred to collectively herein as "anti-T12." These monoclonal antibodies are produced by hybrid cells made using conventional hybridization and screening techniques such as are described in Reinherz et al. (1979) J. Immunol. 123, 1312 and Ritz et al. Nature (1980) 283, 583. As is well-known in the monoclonal antibody field, each independently-produced hybrid cell line which produces a monoclonal antibody specific to the same particular antigenic determinant is nonetheless different from all others, as is each of the monoclonal antibodies so produced. Thus, while repetition of the procedure described in the specific example, below, can result in the production of a hybrid cell line which produces useful anti-T12 monoclonal antibody specific to T12, it is highly unlikely that it will produce a cell line which produces a monoclonal antibody which is chemically an exact copy of the monoclonal antibody described in the example.

A procedure for producing anti-T12 generally involves immunizing mice using tumor cells from a patient suffering from T cell chronic lymphatic leukemia, producing hybrid cells by fusing the spleen cells of the immunized mice to myeloma cells, culturing the cells to produce antibody, and screening the antibody using immunoprecipitation screening to select the hybrid cells which produce monoclonal antibody specifically reactive to the 120,000 dalton surface antigen on T12 mature human T cells and mature human T cell-derived cells.

Another aspect of the invention features the therapeutic use of anti-T12 in the treatment of medical disorders. Such disorders generally are of two major types: (1) immune system disorders involving the patient's own activated or overabundant mature T cells, e.g., autoimmune diseases such as SLE (Lupus), multiple sclerosis (MS), rheumatoid arthritis, juvenile rheumatoid arthritis (JRA) and the rejection of grafted tissue and transplanted organs such as the kidneys, lungs, liver, and heart; and (2) GVHD, caused by the mature T cells of grafted tissue, e.g., bone marrow, or certain transplanted organs such as the liver.

When anti-T12 is used to treat or prevent GVHD caused by the presence of mature T cells in grafted tissue (e.g., bone marrow) or in a transplanted organ, anti-T12 is administered to the patient and/or contacted with the graft or transplant in an amount sufficient to prevent, inhibit, or eliminate GVHD. Anti-T12 is administered to human patients and contacted with transplants mixed with a non-toxic pharmaceutically acceptable carrier substance, most preferably normal saline, and is generaly present in the carrier in a concentration of between about 0.5 µg antibody/ml and 500 µg antibody/ml. The antibody is administered to a patient using any medically appropriate procedure, e.g. intravenous administration. The amount of antibody administered at one time will generally range between about 50 µg and 500 µg of antibody per kg of body weight. It is desirable in some instances to administer the anti-T12 to the patient in a series of more than one administration. It is also sometimes desirable to administer anti-T12 after GVHD symptoms have appeared, rather than immediately following the transplant. Such is the case, for example, when bone marrow is transplanted from an HLA matching donor, and GVHD is not expected to develop.

When the tissue to be grafted or transplanted is contacted with anti-T12 to remove or inactivate mature human T cells, this can be done in a number of ways. One method is to contact the tissue with the antibody in the presence of complement to bring about lysis of the mature T cells. Another method is to covalently bond anti-T12 to a support, e.g. sepharose beads, on a column and then pass the cells of the graft or transplant, in liquid form, through the column. The mature T cells bind to the column and are thus selectively removed from the tissue. This latter procedure has the advantage of obviating the use of complement.

When anti-T12 is administered to a patient in order to treat GVHD, complement is also not needed, because the selective binding of anti-T12 to mature human T cells operates in conjunction with the patient's biological processes to inactivate the mature T cells. The key characteristic of anti-T12 is its ability to selectively bind to mature human T cells and render them inactive in vivo.

The other immunologic characteristics of anti-T12 likewise render it uniquely useful in GVHD therapy. The failure of anti-T12 to modulate T12 means that repeated administrations of anti-T12 are effective to inactivate mature T cells, as would not be the case were modulation to occur. That T12 antigen appears only on the surfaces of mature, and not immature, T cells means that during treatment the mature T cells causing GVHD are inactivated, while immature cells, which are to mature into essential, non-lethal components of the immune system after treatment, are not affected. The failure of anti-T12 to induce lymphocyte activation and proliferation is also important because such capability would be counter-productive in therapy, allowing potentially GVHD-producing lymphocytes to take the place of inactivated cells.

If anti-T12 is used to treat an autoimmune disease or to inhibit the rejection of tissue or organs, rather than to inhibit GVHD, the patient, and not the organ or tissue, is treated with the antibody, because it is the mature T cells of the patient which are to be inactivated. In the case of grafts and transplants, anti-T12 administration can be carried out prior to and/or after transplantation, in one or a series of administrations. The same properties of anti-T12 which render it useful in the treatment of GVHD disease and mature T cell-related disorders such as MS, SLE and JRA make it useful for inhibiting rejection. Anti-T12 is administered to patients to prevent rejection, or to treat disorders such as SLE and JRA, in non-toxic, pharmaceutically acceptable carrier substancies, by means of medically appropriate modes of administration, in the same concentration and dosage ranges discussed above in connection with the treatment of GVHD.

An alternate method for treating disorders involving overabundant or activated mature T cells involves treating the patient's blood, outside the patient, rather than administering the antibody to the patient. Thus a patient suffering from T cell chronic lymphatic leukemia can be treated by having his blood shunted through a T12 column until all of the T12-reactive cancerous cells have been removed from the blood by becoming bound to the column. Multiple sclerosis, in which circulating mature T cells attack the myelinated cells of the central nervous system, can be treated in the same manner. Because the immature T cells are not bound by the column, but remain in the blood, the basis for a new, non-lethal population of T cells remains after treatment.

In another aspect, the invention features the use of anti-T12 to detect or measure mature T cells or cells derived from mature human T cells in a biological sample. Anti-T12 is contacted with the sample and the formation of immunologic complexes between anti-T12 and cells in the sample indicates that those cells are mature human T cells or cells (e.g., certain kinds of tumor cells, such as T cell chronic lymphatic leukemia tumor cells or T cell lymphoma tumor cells) derived from mature human T cells. In liquid samples such as blood or cell homogenates, complexes can be measured using any conventional technique, e.g., using a labelled antibody (labelled with, e.g. a fluorescent compound) capable of binding to anti-T12. Anti-T12 can also be used for in situ analysis of tissue samples, using conventional staining techniques. Such techniques can be used to diagnose practically any disorder caused by overabundant, activated, or malignant mature T cells, including the aforementioned cancers, MS, and JAR, as well as immune disorders, e.g., SCID, characterized by an insufficient number of mature T cells.

Anti-T12 can also be chemically linked to a cytotoxic agent to selectively deliver the toxin to undesired anti-T12 reactive cells, e.g., leukemia cells, without harming other cell types. Such cytotoxic agents can include chemotherapeutic agents, biological toxins such as ricin and mushroom toxins, radioactive agents, and photoactive toxins which are activated by UV light. The photoactive agents can be particularly useful in the treatment of lymphoma tumors appearing at or near the skin surface, where exposure to UV light can be effected easily. Treatment using anti-T12 linked to cytotoxic agents can be carried out in the patient or in tissue, e.g. blood or bone marrow, from the patient or a donor, which is to be put into the patient. Anti-T12 linked to radioactive agents can also be used as a diagnostic tool to label and detect mature T cells or cells derived therefrom.

The following specific examples are intended to more particularly point out the invention, without acting as limitations upon its scope.

EXAMPLE 1

A hybrid cell culture capable of producing a monoclonal antibody specific for the mature human T cell surface antigen T12 was made according to the procedures described in the references cited above, using tumor cells from a patient suffering from T cell chronic lymphatic leukemia to immunize BALB/cJ mice. The steps in carrying out the method were as follows: Two 8 week old female Balb/cJ mice were immunized intraperitoneally with $20 \times 10^6$ tumor cells in phosphate beffered saline. Fourteen days later, a booster injection with $20 \times 10^6$ tumor cells intraperitoneally was performed. Three days before somatic cell fusion of immune splenocytes with NS-1 myeloma cells and 14 days after the booster injection, two mice were injected intravenously and intraperitoneally with a total of $20 \times 10^6$ tumor cells. After the animals were killed, immune splenocytes were obtained, pooled, and fused, employing 30% polyethylene glycol. The fusion product was then plated in multiple microtiter wells as described in the references above. Hybridoma growth was evident by two weeks and supernatants of hybridoma clones were subsequently screened for reactivity by indirect immunofluorescence on a large panel of cell types (T cells, B cells, macrophages, granulocytes, platelets) employing an Epics V fluorescence activated cell sorter. Hybridomas that failed to produce antibodies reactive with tumor were discarded. The remaining reactive supernatants were then screened on the above panel of cell types and those selectively reactive with T cells were selected. These hybridomas of interest were then cloned by limiting dilution and individual hybrids elicited in pristane primed Balb/cJ retired breeder mice. The resulting ascitic fluid was used as a source of antibody. A sample of the new hybrid cell line was deposited in the American Type Culture Collection, Rockville, Maryland, on June 21, 1982, and has been given ATCC accession number 3513.

Isolation of the 120,000 dalton T12 antigen was accomplished by first labelling mature human T cells with $Na^{125}I$. The reaction was catalyzed either by lactoperoxidase or 1,3,4,6-tetrachloro $3\alpha$, $6\alpha$, diphenylglycoluril (Iodogen, Pierce Chemical Co., Il) (Markwell and Fox, 1978). After labelling, cells were lysed with 1% Nonidet P-40 (NP40; Particle Data Laboratories, Elmhurst, IL) in 0.01 ML tris-HCl, pH 7.8, 0.15 M NaCl, lmM PMSF, 0.02 mg/ml ovomucoid trypsin inhibitor (Sigma Chemical Co., St. Louis, MO). The lysates were centrifuged at 13,000 g for 15 min to remove nuclei. The supernatant fluid was centrifuged for 30 min at 100,000 g, then precleared with heat inactivated formalin-fixed *Staphylococcus aureus* (STAPH-A), then subsequently precleared twice with a preformed complex of mouse IgG and rabbit anti-mouse IgG, each for 1 hour at 4° C. Precleared lysates were incubated 3-4 hours with a preformed complex of anti-T12 (isolated and purified as described in Exhibit 4, below) and rabbit anti-mouse immunoglobulin at 4° C. (van Agthoven et al., 1981). The precipitate was resuspended in 0.01 M tris-HCl pH 7.8, 0.15 M NaCl, lmM PMSF, 0.02 mg/ml trypsin inhibitor (Tris-NaCl buffer), and 0.5% deoxycholate sodium salt and washed on a discontinuous gradient consisting of one layer of 10% sucrose, 0.5% NP40 and tris-NaCl buffer, and one layer of 20% sucrose in the same buffer without detergent. After 20 min centrifugation at $30,000 \times g$ at 4° C., the pellet was dissolved in SDS-PAGE sample buffer. Subsequently, SDS polyacrylamide (5-15% gradient) electrophoresis was carred out on the immunoprecipitate on a discontinuous vertical slab gel according to a modification of the procedure described in Laemmli (1980) Nature 227, 680. The internal molecular weight markers were phosphorylase B (94,000 daltons), ovalbumin (43,000 daltons), aldolase (29,000 daltons) and cytochrome C (14,000 daltons).

The anti-T12 monoclonal antibody specifically reactive with T12 antigen was found to be of the IgM isotype, as evidenced by its reactivity with a goat anti-mouse IgM antibody and its lack of reactivity with a goat anti-mouse IgG antibody. Anti-T12 was also found to be unreactive with E-cells, macrophages, and granulocytes.

EXAMPLE 2

The anti-T12 monoclonal antibody of example 1 was used to stain sections of medullary and cortical human thymus tissue. Four $\mu$-thick frozen thymus tissue sections were stained using a four-step peroxidase/antiperoxidase method. Sections were incubated with a 1:500 dilution of ascitic fluid containing anti-T12 for 60 minutes at room temperature, followed by 30 minute incubations with rabbit anti-mouse IgM (N.L. Cappel Laboratories, Inc.), swine anti-rabbit IgG, and finally with peroxidase rabbit-anti-peroxidase reagent (Dakapaths A/H, Copenhagen, Denmark). Each incubation was followed by repeated washing with PBS. Staining was achieved by incubation of sections in an acetate buffered solution (pH 5.0) that contained 3-amino-9 ethyl carbonol (Aldrich Chemical Co., Inc. Milwaukee, WI), dimethylformamide, and hydrogen peroxide. The sections were washed in acetate buffer and mounted in Elvanol.

Anti-T12 membrane-stained virtually all medullary thymocytes, while failing to stain the majority of cortical thymocytes. The few strongly reactive cortical thymocytes were believed to be the aforementioned subpopulation of mature cortical T cells.

EXAMPLE 3

Cortical thymocytes were separated from medullary thymocytes on the basis of PNA reactivity with a fluorescence activated cell sorter utilizing fluorescent labelled PNA. PNA+ and PNA− cells were then stained with anti-T12 using indirect immunofluorescence. Brightly reactive T12+ cells were predominantly concentrated in the PNA− population, although some T12+ cells were found in the PNA+ population.

EXAMPLE 4

This example describes the treatment, using anti-T12, of GVHD in a child who received a bone marrow transplant from an HLA-mismatched donor for the treatment of SCID.

The anti-T12 monoclonal antibody of example 1 was obtained in ascites form from BALB/cJ mice which had been inoculated previously with the T12 hybridoma. This preparation contained greater than 50% specific monoclonal antibody but was contaminated by albumin and normal mouse immunoglobulin. To develop a purified anti-T12 preparation, the monoclonal antibody was separated from the other ascites elements using a standard Sephadex G-200 (Pharmacia) sizing column. With this technique, the immunoglobulin of the IgM isotype was rapidly resolved into a single protein peak. Approximately 20 mg/ml of anti-T12 was obtained per ml of ascites. This material was tested for endotoxin contamination and found to be negative by limulus assay (Microbiological Associates, Walkersville, MD). Routine microbiological cultures did not yield bacteria or fungal contamination. Antibody preparation was stored at −70° C. in sterile 2cc freezing vials. It was thawed, ultracentrifuged at 100,000 g for 20 min to remove immunoglobulin aggregates, and filtered through a 0.22 micron filter prior to clinical usage.

The purified anti-T12 was used in the treatment of a 4 month old female patient who presented with recurrent cough, vomiting, and bilateral otitis media of several months duration. There was also a history of a recent fever and transient maculopapular rash involving the palms and soles. On physical examination the height and weight were within the 50th percentile. There was pus draining from both ears. Respiratory rate was 50/min with mild flaring of the alae nasae. Rhonchi and coarse breath sounds were heard over both lung fields. Chest x-ray revealed bilateral basal infiltrates and absent thymic shadow. Laboratory investigation on admission revealed a total white cell count of 3700/mm$^3$ with 22% lymphocytes. Peripheral blood mononuclear cells contained 44% cells forming rosettes with sheep red cells but failed to proliferate in response to phytohemagglutinin, Concanavalin A, and pokeweed mitogen. Red cells from the child had normal activity for adenosine deaminase and nucleotide phosphorylase. Serum IgG was 80 mg/ml, IgA 15 mg/ml and IgM 14 mg/ml.

The child was placed in a laminar flow unit and given trimethoprim-methasulfizaxozole prophylaxis for *P. carini* and started on a bowel sterilization regimen of oral antibiotics. Three weeks after admission, the child had a 5 day episode of fever, diarrhea, dehydration, and a maculopapular rash. Cytomegalovirus was isolated from the nasopharynx at that time.

Because of the lack of a related HLA matched donor, conventional bone marrow transplantation could not be performed. An attempted reconstitution with irradiated thymus tissue from a 19 week old male abortus was unsuccessful. Several months later (after two attempts at reconstitution without conditioning failed) the patient was conditioned for transplantation with busulfan 8 mg/kg, cytoxan 200 mg/kg, and anti-lymphocytic serum 0.2 mg/kg over 8 days.

Prior to transplantation, the HLA-mismatched maternal bone marrow to be used for the transplant was largely depleted of mature T cells using purified anti-T12, as follows.

Multiple bone marrow aspirates were taken from the patient's mother under general anesthesia. The maternal bone marrow was found to contain about 10% mature T cells. Subsequently, bone marrow mononuclear cells were obtained by Ficoll-Hypaque density centrifugation and washed 4 times to remove residual heparin. The mononuclear cells were then placed in 15 ml sterile plastic tubes (Falcon, Oxnard, CA) and centrifuged at 200g for 5 min. To the mononuclear pellets (20×10$^6$ cells per tube) was added 1 ml of a 1:500 dilution of purified anti-T12 in normal saline. The cells and antibody were vortexed every 10 min gently for 1 hour and subsequently 0.4 cc of rabbit complement (Pelfreeze, Rogers, AK) added to the cells and antibody and the mixture placed at 37° C. for 1 hour. After antibody and complement treatment, cells were washed 3 times to remove dead cells and the entire procedure repeated two times. After the third antibody and complement treatment, cell viability was greater than 99%. Total cell loss did not exceed 30% during this procedure. The treated bone marrow was found to contain less than 0.1% mature T cells, the remainder having been lysed by anti-T12.

The treated bone marrow cells were placed in a final volume of 50 ml in RPMI 1640 (Grand Island Biological Company, Grand Island, NY) and infused into the recipient patient over a 2 hour time period, one day after the cessation of conditioning. Eight days later, a morbilliform rash appeared on the face and spread over the next 5 days to involve the trunk and all extremities. The rash was accompanied by fever, diarrhea, hepatitis, and the development of ascites. A skin biopsy was consistent with acute GVHD. On the second day of the onset of the symptoms (day 10), the child received intravenously, over several hours, anti-T12 at a dose of 100 μg/kg in 50 ml of normal saline containing 1% albumin in an attempt to abort acute GVHD. This infusion was (which employed an infusion sump) was repeated daily for 5 days with complete resolution of signs and symptoms of GVHD by day 15 accompanied by the depletion of mature maternal T cells.

Evidence for hematiogial reconstitution began on day 9 post-transplantation with brisk reticulocytosis. By day 13, WBC increased from <50/mm$^3$ to 1000/mm$^3$ and platelets were >60,000. Immunological function as judged by mitogen proliferation was detected by 3 weeks post-transplant. Following tetanus toxoid immunization at week 4 post-transplant, a specific response to tetanus was detected. At week 5, bone marrow aspiration revealed maternal chromosomes by banding analysis. The patient was discharged 6 weeks post-transplant after recontamination with lactobacillus acidophilus and continued to do well in growth, development, and psychomotor areas.

It was found that, between the fourth and sixth week, the percentage of mature T cells doubled, from 21% to 49%, and a B lymphocyte population was detected for the first time. These developments suggest that the patient underwent normal lymphoid differentiation and acquisition of immune function.

Studies performed after the patient developed immune function showed that the mature T cells circulating in the patient were of maternal origin, but that they were no longer reactive with the child's cells, but had become tolerant to the child's HLA antigens.

We claim:

1. A monoclonal antibody specific to a particular antigen on the surface of mature human T cells,
    said antigen being further characterized in that
        it has a molecular weight of about 120,000 daltons, as determined by carrying out electrophoresis on the antigen and comparing its movement with that of marker proteins of known molecular weight,
        it is not modulated by monoclonal antibodies specific to it, and
        it appears only on the surfaces of mature, and not immature, T cells, and
    said monoclonal antibody being further characterized in that
        it is produced by a hybrid cell comprising a murine lymphocyte,
        it is capable of selectively binding mature human T cells,
        it lyses mature human T cells in vitro in the presence of complement, and
        it fails to induce the proliferation or activation of human lymphocytes.

2. The monoclonal antibody of claim 1 wherein said antibody is further characterized in that it is unreactive with E-cells, macrophages, and granulocytes.

3. The monoclonal antibody of claim 1 wherein said antibody is further characterized in that it is of the IgM isotype.

4. The monoclonal antibody of claim 1, said antibody being produced by the hybrid cell line having the identifying characteristics of ATCC 3513.

5. A therapeutic molecule for the delivery of a cytotoxic agent to unwanted mature human T cells or mature T cell-derived tumor cells comprising the monoclonal antibody of claim 1, chemically linked to said cytotoxic agent.

6. The therapeutic molecule of claim 5 wherein said cytotoxic agent is a chemotherapeutic agent.

7. The therapeutic molecule of claim 5 wherein said cytotoxic agent is a photoactivated toxic agent.

8. The therapeutic molecule of claim 5 wherein said cytotoxic agent is a radioactive agent.

* * * * *

UNITED STATES PATENT OFFICE
CERTIFICATE OF CORRECTION

Patent No. 4,443,427　　　　　　　　　Dated April 17, 1984

Inventor(s) Ellis L. Reinherz et al.

It is certified that error appears in the above-identified patent and that said Letters Patent are hereby corrected as shown below:

Column 5, line 7, "beffered" is changed to --buffered--.

Column 5, line 35, "3513" is changed to --HB8136--.

Column 5, line 39, "3α, 6α" is changed to -- - 3α, 6α- --.

Column 9, line 6, "3513" is changed to --HB8136--.

*Signed and Sealed this*

*Twenty-seventh* Day of *November 1984*

[SEAL]

*Attest:*

GERALD J. MOSSINGHOFF

*Attesting Officer*　　　*Commissioner of Patents and Trademarks*